United States Patent
Toraya et al.

(10) Patent No.: US 6,873,681 B2
(45) Date of Patent: Mar. 29, 2005

(54) METHOD OF ESTIMATING PREFERRED ORIENTATION OF POLYCRYSTALLINE MATERIAL

(75) Inventors: Hideo Toraya, Tachikawa (JP); Kazuhiko Omote, Akiruno (JP)

(73) Assignee: Rigaku Corporation, Akishima (JP)

( * ) Notice: Subject to any disclaimer, the term of this patent is extended or adjusted under 35 U.S.C. 154(b) by 136 days.

(21) Appl. No.: 10/441,613

(22) Filed: May 20, 2003

(65) Prior Publication Data

US 2003/0235270 A1 Dec. 25, 2003

(30) Foreign Application Priority Data

May 23, 2002 (JP) .......................... 2002-149097
Dec. 5, 2002 (JP) .......................... 2002-353282

(51) Int. Cl.$^7$ ............................................. G01N 23/20
(52) U.S. Cl. ............................................. 378/71
(58) Field of Search ........................................ 378/71

(56) References Cited

FOREIGN PATENT DOCUMENTS

JP 05-001999 1/1993

OTHER PUBLICATIONS

James, R. W., "The Optical Principles of the Diffraction of X–Rays." G. Bell and Sons LTD., London, (1967), pp. 34–52.

Dollase, W.A., "Correction of Intensities for Preferred Orientation in Powder Diffactometry: Application of the March Model." J. Appl. Cryst. (1986), vol. 19, pp. 267–272.

Seabaugh M, M., et al., "Comparison of texture analysis techniques for highly oriented alpha–A1203" Journal of the American Ceramic Society, vol. 83, No. 8, Aug. 2000, pp. 2049–2054, XP002299301 USA.

Vaudin M. D., et al., "A method for crystallographic texture investigation using standard s–ray equipment" Journal of Materials Research, vol., 13, No. 10, Oct. 1998, pp. 2910–2919, XP002299493 USA.

Neerinck, D. G., et al. "Depth Profiling of thin Ito films by grazing incidence x–ray diffraction" Thin Solid Films, Elselvier–Sequoia S.A. Lausanne, CH, vol. 278, No. ½, May 15, 1996, pp. 12–17, XP000637212, ISSN: 0040–6090.

*Primary Examiner*—Craig E. Church
*Assistant Examiner*—Jurie Yun
(74) *Attorney, Agent, or Firm*—Frishauf, Holtz, Goodman & Chick, P.C.

(57) ABSTRACT

The preferred orientation of a polycrystalline material is estimated using one diffraction peak. An orientation density distribution function $\rho$ is assumed to be axisymmetric around a normal direction of the surface of a sample made of a polycrystalline material. The function $\rho$ may be a Gaussian function or a March-Dollase function. An X-ray is incident upon the surface of the sample at an incident angle $\alpha$ and the intensity of a diffraction X-ray is measured. The change of intensity of the diffraction X-ray is measured with the incident angle $\alpha$ being changed to attain a measurement rocking curve. A theoretical diffraction X-ray intensity is calculated based on the orientation density distribution function $\rho$. The characteristic parameter of the function $\rho$ is determined so that the theoretical rocking curve approaches the measurement rocking curve as closely as possible, whereby the orientation density distribution function $\rho$ can be determined.

9 Claims, 22 Drawing Sheets

Fig. 4

ORIENTATION PROBABILITY $$\rho(\phi, \xi) \sin\phi \, d\xi \, d\phi \qquad \cdots (1)$$

GAUSSIAN FUNCTION $$\rho(\phi, \xi) = G \exp\left[-4\ln 2 \left(\frac{\phi}{H}\right)^2\right] \qquad \cdots (2)$$

$$G = \left\{2\pi \int_0^{\pi/2} \exp\left[-4\ln 2 \left(\frac{\phi}{H}\right)^2\right] \sin\phi \, d\phi\right\}^{-1} \qquad \cdots (3)$$

$$G = \frac{2\sqrt{\ln 2}}{\pi^{3/2} H} \left[\text{Im}[w(x)] - \exp\left(-\frac{\pi^2 \ln 2}{H^2}\right) \text{Re}[w(z)]\right]^{-1} \qquad \cdots (4)$$

Fig. 5

$$w(z) = \exp(-z^2) \frac{2}{\sqrt{\pi}} \int_{-iz}^{\infty} \exp(-t^2) dt \quad \cdots (5)$$

$$z = x + iy = \frac{H}{4\sqrt{\ln 2}} + i \frac{\pi \sqrt{\ln 2}}{H} \quad \cdots (6)$$

MARCH-DOLLASE FUNCTION $$\rho(\phi, \xi) = \frac{1}{2\pi} \left[ r^2 \cos^2 \phi + \frac{1}{r} \sin^2 \phi \right]^{-3/2}$$

$$\cdots (7)$$

DIFFRACTION INTENSITY $$\frac{P}{I} = 2\Psi pN \rho(\phi) \int \overline{P}(\theta) d\theta \quad \cdots (8)$$

$$= \frac{pLQ}{2R\sin\theta_0} \rho(\phi) V \quad \cdots (9)$$

DETECTION RANGE $$2\Psi = \frac{L}{2R\sin\theta_0} \quad \cdots (10)$$

Fig. 6

VOLUME FRACTION OF CRYSTALLITE $$\int_0^{2\pi} \int_0^{\Theta} \rho(\phi, \xi) \sin\phi \, d\xi \, d\phi \qquad \cdots (11)$$

$$Q = \frac{N_0^2 \lambda^3}{\sin 2\theta_0} |F(hkl)|^2 \left[\frac{e^2}{mc^2}\right]^2 \frac{1+\cos^2 2\theta_0}{2} \qquad \cdots (12)$$

$$V = \left[1 + \frac{\sin\alpha}{\sin\beta}\right]^{-1} \times \left\{1 - \exp\left[-\frac{\rho'}{\rho}\mu t\left(\frac{1}{\sin\alpha} + \frac{1}{\sin\beta}\right)\right]\right\} \frac{S_0}{\mu} \qquad \cdots (13)$$

RANDDOM ORIENTATION $\rho(\phi)$ = GAUSSIAN FUNCTION $CeO_2$ POWDER (220)

$\lambda = 0.12nm$

STRONG ORIENTATION  H = 3.32°

$\rho(\phi)$ = GAUSSIAN FUNCTION

Au THIN FILM (002)

CuK$\alpha$

Fig. 14

| SAMPLE | WAVE-LENGTH $\lambda$ (nm) | GAUSSIAN FUNCTION | | | MARCH-DOLLASE | | |
|---|---|---|---|---|---|---|---|
| | | H (°) | $\theta_0$ (°) | v (%) | r | $\theta_0$ (°) | v (%) |
| Au(111) 30nm | 0.12 | 81 | 15.54 | 97.6 | 0.79 | 15.50 | 88.3 |
| | CuKα | 89 | 19.87 | 99.7 | 0.82 | 20.1 | 98.9 |
| Au(111) 50nm | 0.12 | 30.9 | 14.92 | 93.9 | 0.496 | 14.90 | 49.6 |
| | CuKα | 32.3 | 19.23 | 94.0 | 0.511 | 19.23 | 49.9 |
| AlN(002) | CuKα | 3.32 | | 93.8 | 0.085 | | 61.0 |

SINGLE LAYER MODEL

TWO-LAYER MODEL

MULTI-LAYER MODEL

Fig. 16

TWO-LAYER MODEL $$\frac{P}{I} = \frac{pLQ}{2R\sin\theta_0}[\rho(\phi)_U V_U + \rho(\phi)_L V_L] \quad \cdots(14)$$

$$V_U = \left\{\left[1+\frac{\sin\alpha}{\sin\beta}\right]^{-1} \times \left\{1 - \exp\left[-\eta\frac{\rho'}{\rho}\mu t\left(\frac{1}{\sin\alpha}+\frac{1}{\sin\beta}\right)\right]\right\}\right\}\frac{S_0}{\mu} \quad \cdots(15)$$

$$V_L = \left\{\left[1+\frac{\sin\alpha}{\sin\beta}\right]^{-1} \times \left\{\exp\left[-\eta\frac{\rho'}{\rho}\mu t\left(\frac{1}{\sin\alpha}+\frac{1}{\sin\beta}\right)\right] - \exp\left[-\frac{\rho'}{\rho}\mu t\left(\frac{1}{\sin\alpha}+\frac{1}{\sin\beta}\right)\right]\right\}\right\}\frac{S_0}{\mu} \quad \cdots(16)$$

Fig. 17

MULTI-LAYER MODEL $$\frac{P}{I} = \frac{pLQ}{2R\sin\theta_0} \sum_{m}^{M} \rho(\phi)_m V_m \quad \cdots(17)$$

$$V_m = \left[1 + \frac{\sin\alpha}{\sin\beta}\right]^{-1} \times \left\{\exp\left[-\frac{\rho'}{\rho}\mu(m-1)\Delta t\left[\frac{1}{\sin\alpha} + \frac{1}{\sin\beta}\right]\right]\right.$$
$$\left. - \exp\left[-\frac{\rho'}{\rho}\mu m \Delta t\left[\frac{1}{\sin\alpha} + \frac{1}{\sin\beta}\right]\right]\right\} \frac{S_0}{\mu} \quad \cdots(18)$$

CONTINUOUS MODEL

LINEAR MODEL $\quad H_m = a + bz_m \quad \cdots(19)$

CURVED LINE MODEL $\quad H_m = c/(d - z_m) \quad \cdots(20)$

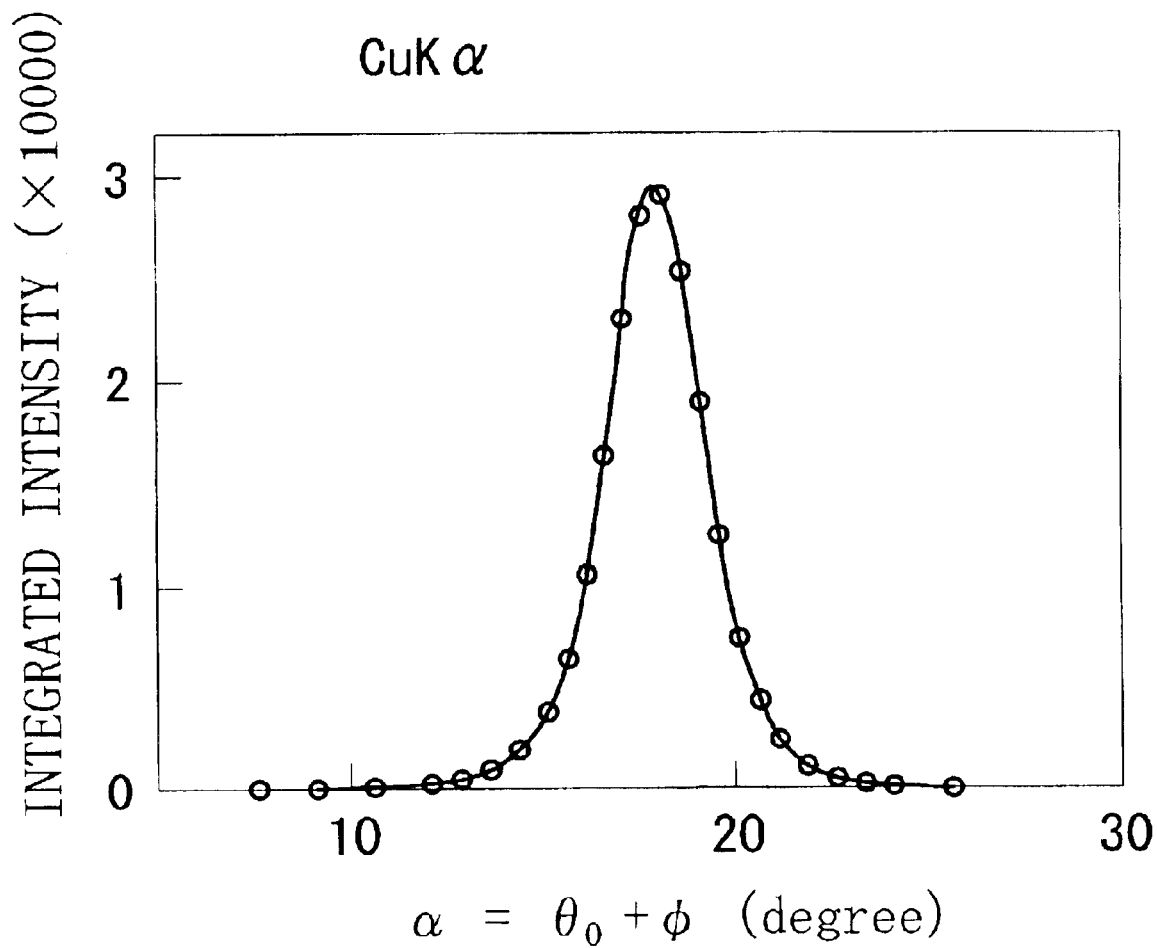

Fig. 20

SINGLE LAYER MODEL

|    | $R_p$ | $R_{wp}$ | $H(°)$ |
|----|-------|----------|--------|
| SR | 0.095 | 0.146    | 3.38   |
| LX | 0.074 | 0.132    | 3.32   |

TWO-LAYER MODEL

|    | $R_p$ | $R_{wp}$ | $H_U(°)$ | $H_L(°)$ | $\eta$ |
|----|-------|----------|----------|----------|--------|
| SR | 0.010 | 0.020    | 2.59     | 5.03     | 0.47   |
| LX | 0.014 | 0.026    | 2.81     | 5.67     | 0.59   |

Fig. 21

| CONTINUOUS MODEL | | $R_p$ | $R_{wp}$ | a | b | c | d |
|---|---|---|---|---|---|---|---|
| LINEAR MODEL | SR | 0.013 | 0.025 | 1.81 | -4.1 | | |
| | LX | 0.018 | 0.039 | 1.86 | -4.1 | | |
| CURVED LINE MODEL | SR | 0.016 | 0.029 | | | 3.12 | 1.39 |
| | LX | 0.003 | 0.011 | | | 3.04 | 1.356 |

Fig. 22

ESTIMATION INDEXES $$R_{wp} = \left[ \frac{\Sigma_i w_i \{y_i - f_i(x)\}^2}{\Sigma_i w_i y_i^2} \right]^{1/2} \quad \cdots (21)$$

$$R_p = \frac{\Sigma_i |y_i - f_i(x)|}{\Sigma_i y_i} \quad \cdots (22)$$

METHOD OF ESTIMATING PREFERRED ORIENTATION OF POLYCRYSTALLINE MATERIAL

BACKGROUND OF THE INVENTION

1. Field of the Invention

The present invention relates to a method of estimating the preferred orientation of a polycrystalline material using an X-ray diffraction method.

2. Description of the Related Art

Methods of estimating the preferred orientation of a polycrystalline material utilizing X-ray diffraction phenomena include a qualitative technique through measurement of the full width of half maximum in a rocking curve, and a quantitative technique in which the orientation distribution function (ODF) is calculated with the use of pole measurement.

According to the former technique by which the full width of half maximum is determined, there are problems in that the preferred orientation can not be quantitatively determined, and such a weak preferred orientation as to exhibit no peak in the rocking curve can not be estimated. But, this technique still has been practically used, in which a lot of samples are measured with the same measuring apparatus under the same measurement conditions, and the obtained full widths of half maximum are relatively compared with each other. However, it is very difficult to compare the full widths of half maximum, which are determined with different measuring apparatus or under the different measurement conditions, with each other. Because the full widths of half maximum depend on measurement optical systems so that the reliability of the absolute values is low.

The latter pole measurement technique has problems in that a goniometer having a complicated structure including a $\chi$ axis is required, and it takes much time to measure. Also, in this case, weak orientation can not be quantitatively estimated, because of the correction of an X-ray irradiation area and the complicated calculation of the back ground.

Japanese Patent Publication No. 5-1999 A (1993) discloses a technique which uses a theoretical diffraction intensity calculation formula. This technique is, however, limited to the estimation of the change in the degree of preferred orientation in the direction of a sample thickness, and accordingly the changes in the degree of preferred orientation in the preferred orientation of a sample itself can not be absolutely quantified.

SUMMARY OF THE INVENTION

To solve the above-described problems, the present invention has been devised. It is an object of the present invention to provide a method of estimating the preferred orientation of a polycrystalline material by which the preferred orientation can be quantitatively estimated, and the degree of preferred orientation can be clearly determined even for weak orientation, using one diffraction peak and depending neither measuring apparatuses nor measurement conditions.

The method of estimating the preferred orientation of a polycrystalline material according to the present invention includes the steps of: (a) assuming an orientation density distribution function $\rho$ which is axisymmetric on a normal direction of a surface of a sample made of a polycrystalline material, said orientation density distribution function $\rho$ being a function of an angle $\phi$ at which a normal of a measurement lattice plane of a crystallite of the sample is inclined to the normal of the surface of the sample, and said orientation density distribution function $\rho$ containing a characteristic parameter characterizing a form of the function; (b) measuring an intensity of a diffraction X-ray incident upon the surface of the sample at an incident angle $\alpha$ and reflected from said measurement lattice plane of the sample, and determining a change of the intensity of the diffraction X-ray from said measurement lattice plane with the incident angle $\alpha$ being changed to obtain a measurement rocking curve, wherein the diffraction X-ray from the measurement lattice plane has an angle $2\theta_0$ to an incident X-ray, and the incident angle $\alpha$ has a relationship of $\alpha=\theta_0+\phi$; (c) calculating a theoretical diffraction X-ray intensity based on said orientation density distribution function $\rho$ to obtain a theoretical rocking curve including said characteristic parameter; and (d) determining said characteristic parameter so that said theoretical rocking curve approaches said measurement rocking curve as closely as possible, whereby said orientation density distribution function $\rho$ is determined.

In the step of obtaining the measurement rocking curve, the measured values are not necessarily connected to each other through a curve. Discontinuous measured value will do as long as the fitting operation with the theoretical rocking curve can be performed The present invention has the advantages that the preferred orientation can be quantitatively estimated, and the degree of the preferred orientation can be clearly determined even for a weak orientation, using one diffraction peak and depending on neither nor the measurement conditions.

BRIEF DESCRIPTION OF THE DRAWINGS

FIG. 4 shows equations which are in relation to an orientation density distribution function;

FIG. 5 shows equations which are in relation to the orientation density distribution function and a diffraction intensity;

FIG. 6 shows equations which are in relation to the diffraction intensity;

FIG. 14 is a list of measurement results;

FIG. 16 shows equations which are in relation to a diffraction intensity in the two-layer model;

FIG. 17 shows equations which are in relation to diffraction intensities in the multi-layer model and the continuous model;

FIG. 18 is a graph, similar to that of FIG. 11, for the two-layer model;

FIG. 20 is a list of estimation results of the preferred orientation in the single layer model and the two-layer model;

FIG. 21 is a list of estimation results of the preferred orientations for the linear model and the curved line model of the continuous model; and FIG. 22 shows equations of estimation indexes.

DETAILED DESCRIPTION OF THE PREFERRED EMBODIMENTS

Figure 1:
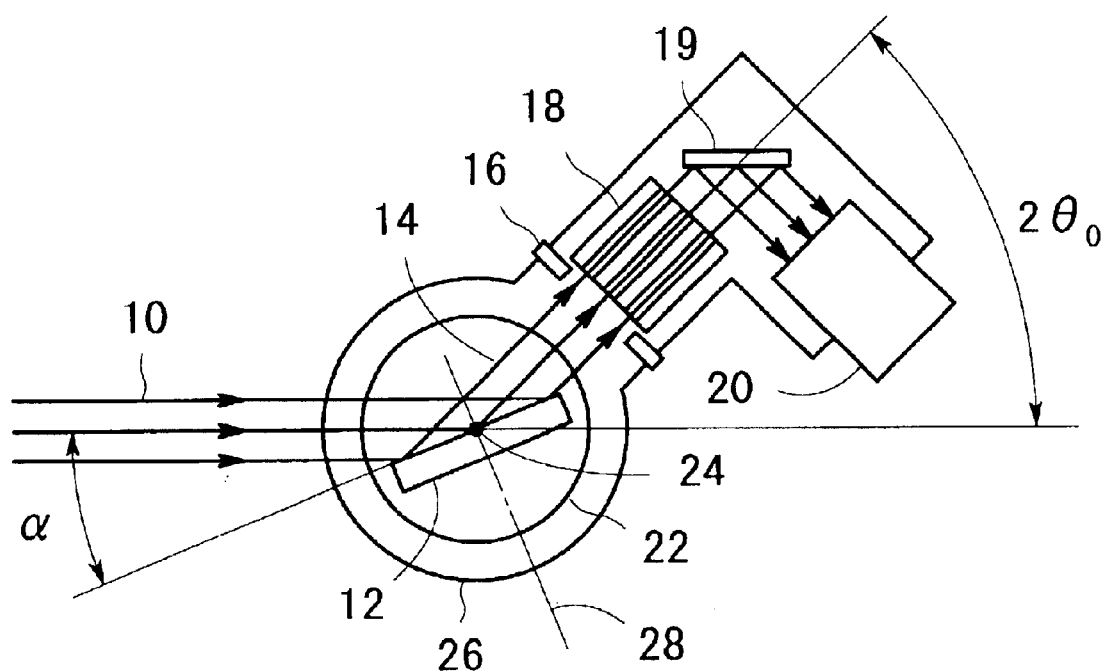
FIG. 1 is a plan view of an embodiment of an X-ray diffraction apparatus for use in carrying out the present invention.

First, a method for determining a measurement rocking curve will be described. FIG. 1 is a plan view of an embodiment of an X-ray diffraction apparatus for use in carrying out the present invention. An incident X-ray 10 consisting of a parallel X-ray beam is incident upon the surface of a sample 12 at an incident angle $\alpha$. The diffraction X-ray reflected from the sample 12 passes through a receiving slit 16 and a Soller slit 18, and is reflected by a crystal analyzer 19, Ge(111), and is then detected by an X-ray detector 20. Thus, this X-ray diffraction apparatus is operated in a parallel beam method. Since the crystal analyzer 19 is used in addition to the Soller slit 18, a higher resolution is realized. Two kinds of X-ray sources, i.e., a synchrotron radiation and an X-ray tube, are used in the measurement examples described below. The crystal analyzer 19 is employed, as shown in FIG. 1, only when the synchrotron radiation is used. When the X-ray tube is used, the crystal analyzer 19 is omitted, and the X-ray passing through the Soller slit 18 is directly incident upon the X-ray detector 20. This is because, in the use of the X-ray tube, a sufficient X-ray detection intensity can not be attained with the use of the crystal analyzer 19.

The receiving system (the receiving slit 16, the Soller slit 18, the crystal analyzer 19 and the X-ray detector 20) is arranged at an angle $2\theta_0$ with respect to the incident X-ray 10. The Bragg angle, which depends on the wavelength of the incident X-ray 10, of the measurement lattice plane of the sample 12 is $\theta_0$. The sample 12 is placed on a sample rotary stage 22. The sample rotary stage 22 can be rotated around the center 24, which is perpendicular to the paper sheet of FIG. 1, of a goniometer. Moreover, the sample 12 can be rotated around a horizontal axis of rotation 28 which is perpendicular to the center 24 of the goniometer, that is, the sample 12 can take an in-plane rotation. The receiving system is placed on the detector rotary stage 26. The detector rotary stage 26 can be also rotated around the center 24 of the goniometer.

Figure 2A:
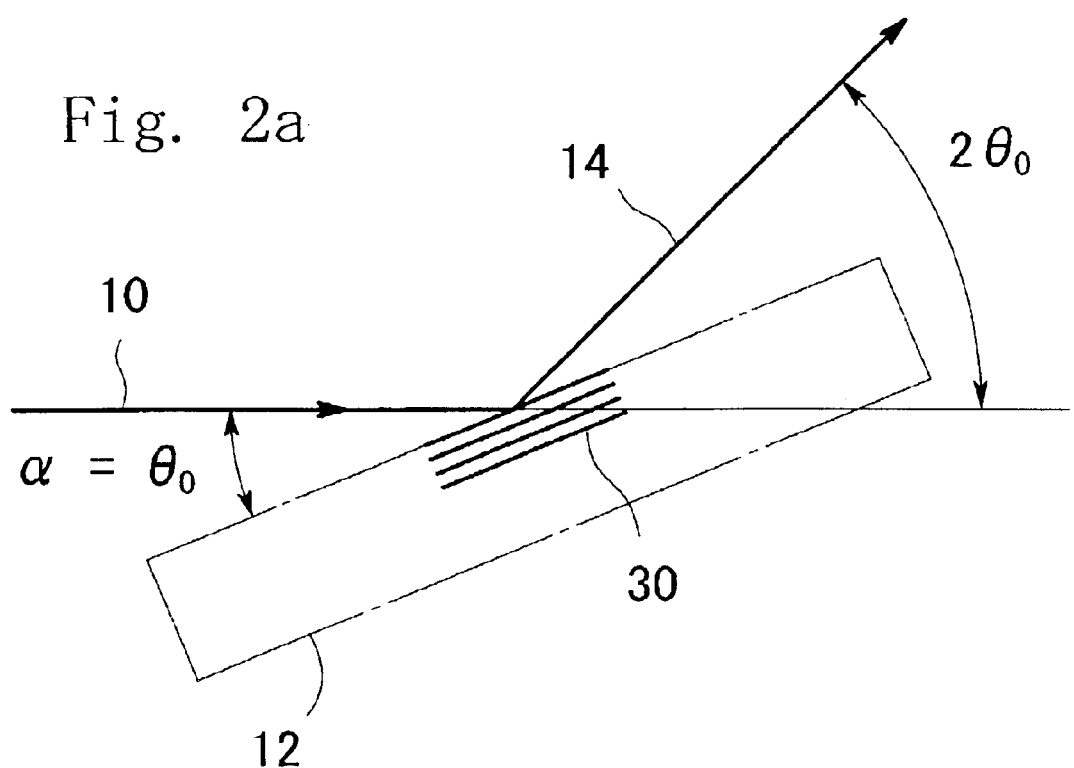
FIGS. 2a and 2b illustrate the different states in which an X-ray is diffracted on a measurement lattice plane in a sample.
Figure 2B:
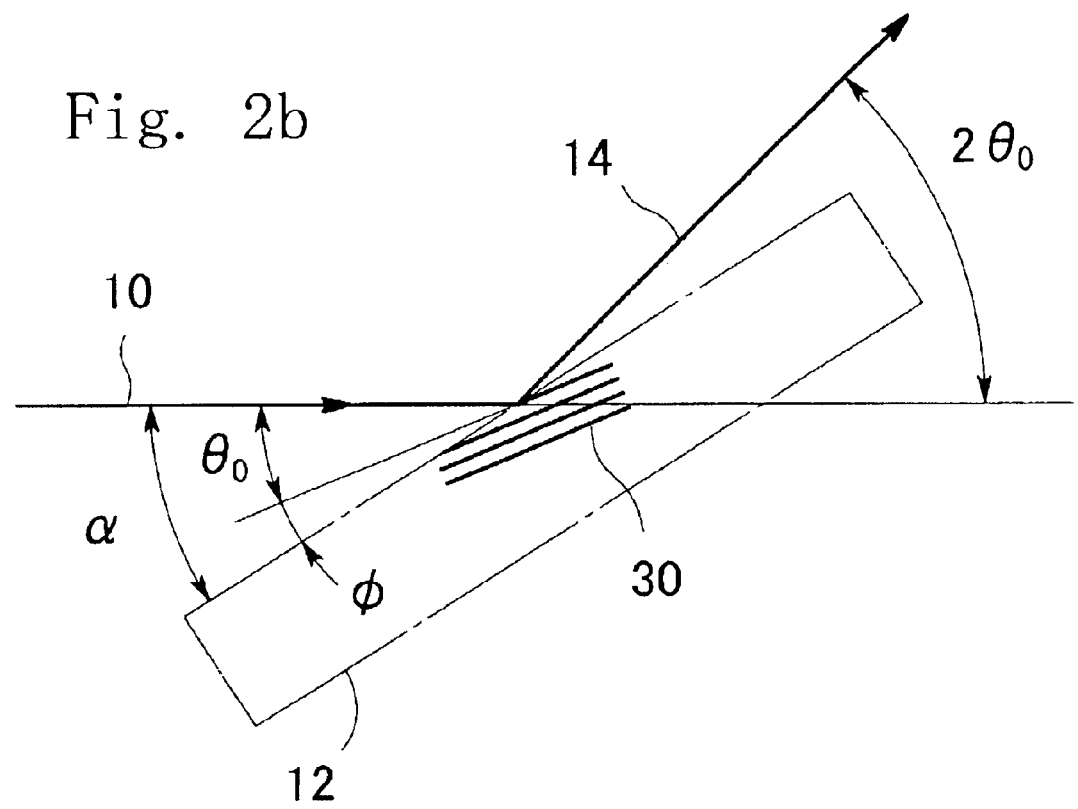

The above-mentioned Bragg angle $\theta_0$ can be decided by selecting the measurement lattice plane of the sample 12 and the wavelength of the used X-ray. Referring to FIG. 2a, when the incident angle $\alpha$ is equal to $\theta_0$, the measurement lattice plane 30, which contributes to the diffraction, is parallel to the surface of the sample 12. Naturally, the normal of the measurement lattice plane 30 is parallel to the normal of the sample surface. In other words, only the crystallite that has the measurement lattice plane parallel to the sample surface contributes to the diffraction. The diffraction X-ray from the above-mentioned crystallite will be detected. On the other hand, in FIG. 2b, when the sample 12 is rotated by an angle $\phi$, that is, the incident angle $\alpha=\theta_0+\phi$, only the crystallite inclined to the sample surface by an angle $\phi$ contributes to the diffraction. As described above, when the detector is fixed at the position of $2\theta_0$ while the sample 12 is rotated, the incident angle $\alpha$ is changed. As a result, there can be obtained diffraction X-ray intensity information for the different crystallites which correspond to respective inclination angles $\phi$, that is, different crystallite oriented by different angles $\phi$ with respect to the sample surface.

In the present invention, since the orientation density distribution function $\rho$ is assumed to be axisymmetric around the normal direction of the sample surface, the sample takes an in-plane rotation during the measurement of the diffraction intensity. Thereby, the theoretical rocking curve and the measurement rocking curve can be compared with each other. It is to be noted that if the preferred orientation of a sample is expected to be axisymmetric, the in-plane rotation of the sample may be omitted.

Figure 7:
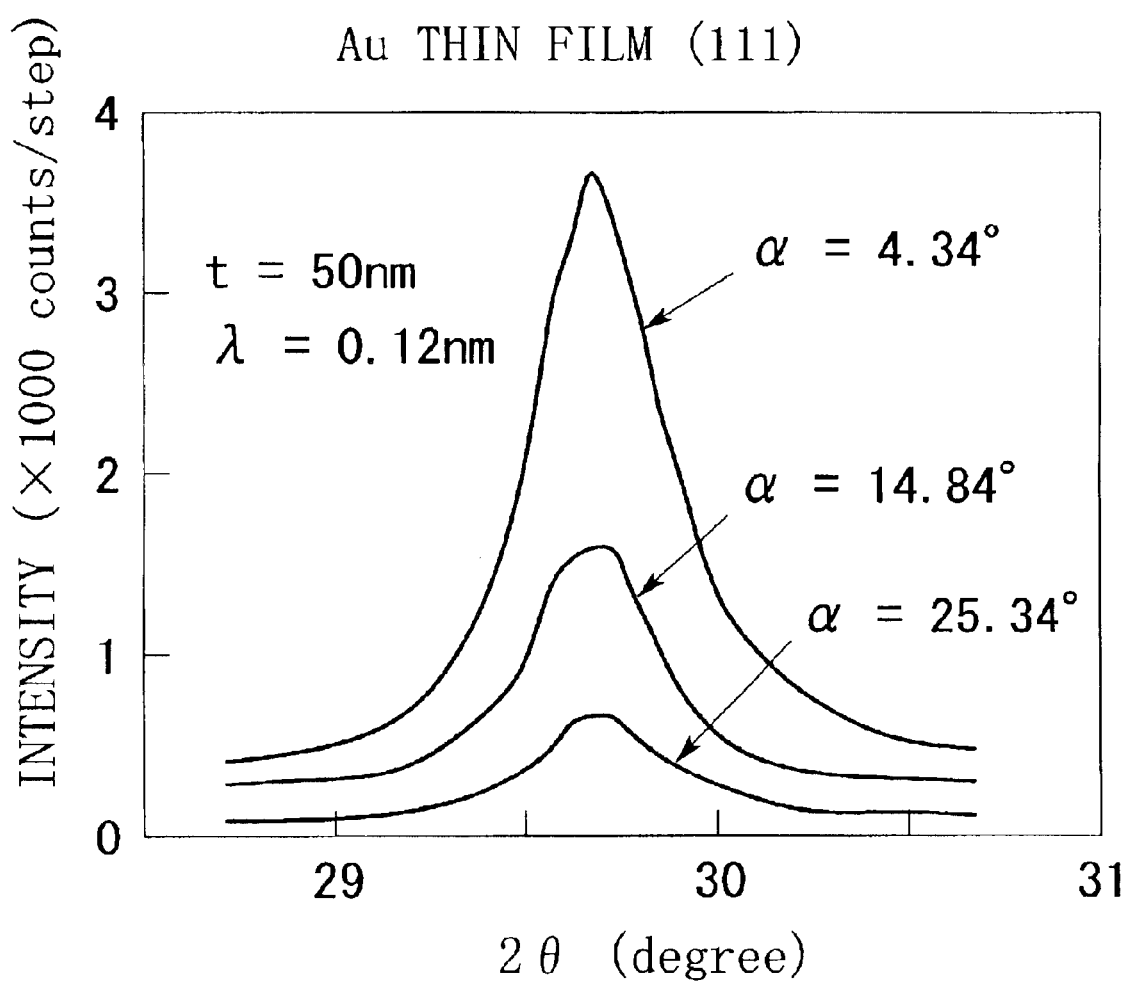
FIG. 7 is a graph for use in determination of an integrated intensity.
Figure 8:
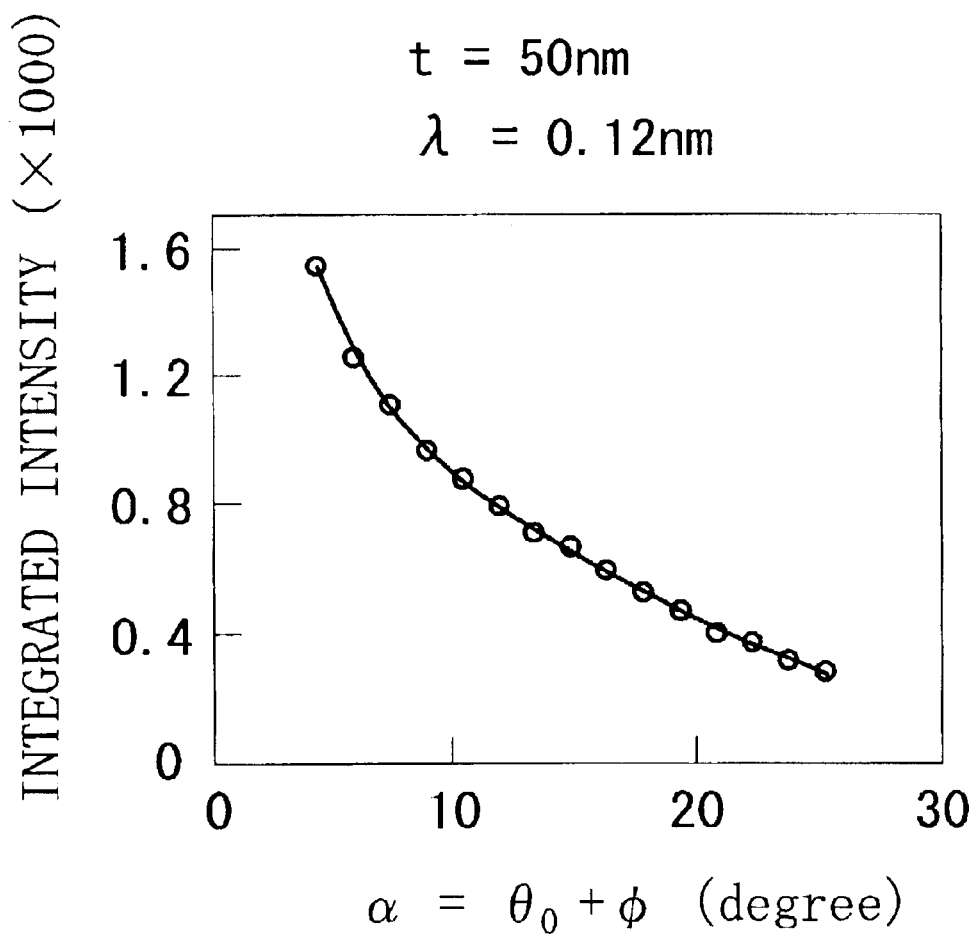
FIG. 8 is a graph of a measurement for the (111) reflection of an Au thin-film with a thickness of 50 nm.

As described above, the diffraction X-ray intensity P is measured with the incident angle $\alpha$ being changed while the position of the detector is fixed at $2\theta_0$, so that an $\alpha$-P rocking curve can be obtained. To accurately determine the diffraction X-ray intensity, it is preferable to obtain the integrated intensity of a diffraction peak as described below. That is, the receiving system is scanned around the angle $2\theta_0$ while a certain incident angle $\alpha$ is fixed, so that a peak profile as shown in FIG. 7 can be obtained. FIG. 7 is a graph of a measurement for the (111) reflection of a polycrystalline thin film of Au (gold) having a thickness of 50 nm. The X-ray source is a synchrotron radiation and an X-ray with a wavelength of 0.12 nm are taken out. The peak profiles shown in the graph can be obtained by scanning the receiving system around $2\theta_0$ while the incident angle $\alpha$ is fixed, e.g., 4.34°. An accurate diffraction X-ray intensity can be obtained by determination of the area of the peak profile, that is, determination of the integrated intensity. The determined integrated intensity corresponds to the data appearing as the leftmost blank circle in the graph of FIG. 8, the integrated intensity at $\alpha=4.34°$. Thus, in the similar way, the integrated intensities can be determined for other $\alpha$ values, e.g., at $\alpha=14.84°$ and $\alpha=25.34°$. In the practical measurement, the integrated intensities of diffraction X-rays at a number of incident angles a at desired angular intervals are determined, so that the blank circles as shown in FIG. 8 can be obtained. These data show the measurement rocking curve. It should be noted that the solid line in FIG. 8 is not the measurement rocking curve but a theoretical rocking curve which is described below.

Figure 3:
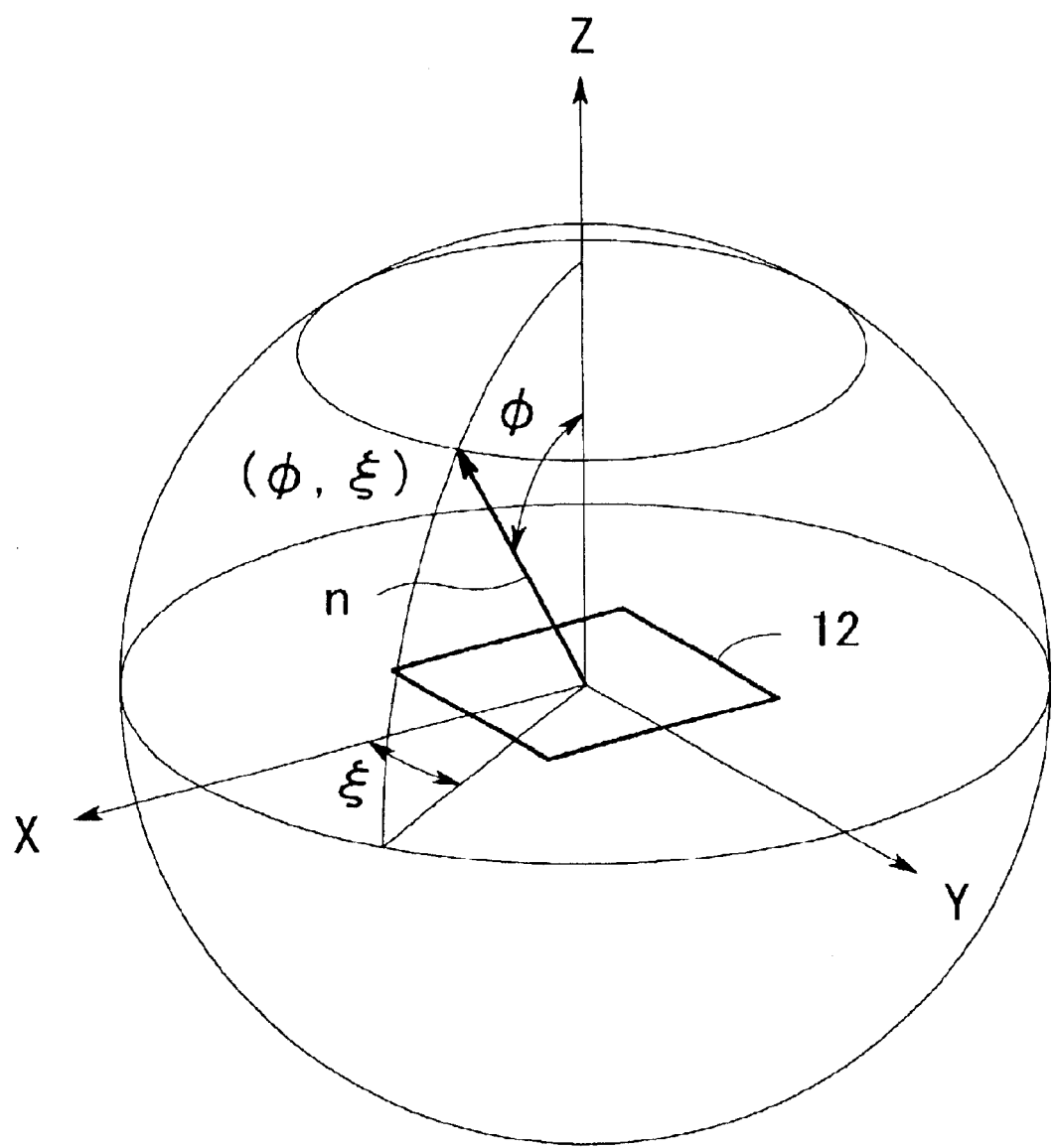
FIG. 3 is a perspective view of spherical coordinates by which the normal vector of the measurement lattice plane of a crystallite is expressed.

Next, a method of determining the theoretical rocking curve will be described. FIG. 3 is a perspective view of spherical coordinates showing a normal vector n of the measurement lattice plane of a crystallite. The X-Y plane is assumed to be on the surface of the sample 12, and the Z-axis extends in the normal direction of the sample surface. The normal vector n of the measurement lattice plane of the crystallite can be expressed by spherical coordinates $(\phi, \xi)$. The angle $\phi$ is an angle with which the normal vector n is inclined from the Z-axis which is the normal of the sample surface. The angle $\xi$ is an azimuth from the X-axis when the normal vector is projected onto the X-Y plane.

In general, the orientation density distribution function $\rho$ of a crystallite having a normal vector n is a function of $\phi$ and $\xi$, i.e., $\rho=\rho(\phi, \xi)$. The probability with which there exists a crystallite having a normal vector in the ($\phi$, $\xi$) direction, orientation probability, is expressed by equation (1) in FIG. 4. For a polycrystalline material which is oriented completely at random, $\rho$ would be constant. It is now assumed that the functional form of $\rho$ is an axisymmetric on the Z-axis. Then, the $\rho$ does not depend on $\xi$, and is a function of $\phi$ only. In the embodiment of the present invention, a Gaussian function and a March-Dollase function are used as the orientation density distribution function $\rho$ to determine a theoretical rocking curve.

The Gaussian function is expressed by equation (2) in FIG. 4. The symbol G in equation (2) is a normalizing factor, which can be calculated by equation (3) and then expressed by equation (4). In equation (4), Re[w(z)] and Im [w(x)] are the real part and the imaginary part of a scaled complex complementary error function w(z), respectively. The function w(z) is expressed by equation (5) in FIG. 5. The variable z is expressed by equation (6).

In equation (2), H is the full width of half maximum of the Gaussian function, and has a dimension of angle. The H is a characteristic parameter which characterizes the functional form of the Gaussian function. Accordingly, when the H is determined, the functional form of $\rho(\phi)$ is determined. When the functional form is determined, the theoretical diffraction X-ray intensity can be calculated as described below.

On the other hand, the March-Dollase function is expressed by equation (7) in FIG. 5. In equation (7), r is a preferred orientation coefficient, for more details see Dollase: J. Appl. Cryst. (1986), 19, 267–272. The r is a characteristic parameter for the March-Dollase function.

The ratio P/I in which P is a diffraction X-ray intensity and I is an incident X-ray intensity is expressed by equation (8) in FIG. 5, for more details see R. W. James: "The Optical Principles of the Diffraction of X-rays", (1967), Bell, London. In equation (8), N is the number of crystallites in a unit volume of a sample, p is the duplication degree of reflection, and P($\theta$) having a lateral bar over P is an average reflection ability of crystallites. 2$\psi$ is an angle range, the angle range in the direction perpendicular to the paper sheet of FIG. 1, in which there exists a scattering vector relating to an observed diffraction intensity. The 2$\psi$ can be calculated by equation (10) in FIG. 5. In equation (10), L is the length of the receiving slit 16 (see FIG. 1), that is, an aperture length in the direction perpendicular to the paper sheet of FIG. 1, and R is the distance between the center 24 of a goniometer and the receiving slit 16. Eventually, equation (8) can be changed to equation (9). In equation (9), Q and V can be calculated by equations (12) and (13), respectively. In equation (12), $N_0$ is the number of unit cells per unit volume, F(hkl) is a structure factor, e and m are the charge and the mass of an electron, respectively, and c is a light velocity in a free space. In equation (13), $\rho'$ is the density of a thin film, $\rho$ is the density of a bulk crystal, $\mu$ is a linear absorption coefficient, t is the thickness of a sample layer, and $S_0$ is the cross-sectional area of an incident beam. Then, $\alpha=\theta_0+\phi$ and $\beta=\theta_0-\phi$ are effective.

If the functional form of $\rho(\phi)$ is determined, P/I can be calculated with the use of equations (2), (7) to (9), (12), and (13). In equation (9) calculating P/I, only $\rho(\phi)$ and V (excluding $S_0/\mu$) affect the form of the theoretical rocking curve, see equation (2) or (7) for $\rho(\phi)$ and see equation (13) for V. The other variables (pLQ/2Rsin $\theta_0$) would affect the overall intensity of the rocking curve only. Thus, these parts, pLQ/2Rsin $\theta_0$, can be substituted by a scale factor C in calculating the intensity. The function $\rho(\phi)$ includes the characteristic parameter which becomes a variable. The functional form can be changed by changing the characteristic parameter. Accordingly, the characteristic parameter and the scale factor can be determined so that the theoretical rocking curve, the theoretical $\phi$ P curve, agrees with the measurement rocking curve. With the obtained characteristic parameter, the orientation density distribution function $\rho$ representing the preferred orientation of the polycrystalline material can be determined. The scale factor C makes the overall intensity up and down only, having no relation to the preferred orientation. Therefore, in the measurement results described below, only the values of the characteristic parameter are shown without reference to the scale factor value. When the form of $\rho$ is determined as described above, there can be determined the volume fraction with which the normals of the measurement lattice planes of crystallites exist within the range of the inclination angle $\Theta$ from the normal of the sample surface. Stating in details, integrating the orientation density distribution function $\rho$ with respect to the inclination angle $\phi$ from zero to a desired angle $\Theta$ results in the volume fraction of crystallites with which the normals of the measurement lattice planes exist within the angle range from the normal direction of the sample surface to the angle inclined by the angle $\Theta$ from the normal direction.

Next, specific measurement examples will be described. FIG. 8 is a graph of a measurement for the (111) reflection of a polycrystalline thin film of Au (gold) having a thickness of 50 nm and formed by sputtering on a glass substrate. The X-ray source is a synchrotron and an X-ray with a wavelength of 0.12 nm is taken out. The Bragg angle $\theta_0$ is 14.76°. The blank circles in the graph represent integrated intensities for the respective incident angles $\alpha$ determined as described in FIG. 7. In the graph, the solid line represents the theoretical rocking curve, in which the orientation density distribution function $\rho(\phi)$ is assumed to be a Gaussian function and the full widths of half maximum of the Gaussian distribution are so determined that they agree with the measurements, blank circles. The H becomes 30.9°. In this case, curve fitting is carried out with the use of the method of least squares, more specifically, the Gaussian-Newton method. The measurements are sufficiently in agreement with the theoretical curve. It should be noted that it can not be apparently seen whether the material is oriented or not by observing the rocking curve in the graph. However, the analysis according to this invention reveals that the curve is apparently different from that of an unoriented material. As a result, it is seen quantitatively that this material is slightly oriented.

The method of estimating the preferred orientation of a polycrystalline material according to the invention has the advantages in that the quantitative estimation of a preferred orientation can be carried out by using one diffraction peak and depending on neither measuring apparatus nor measurement conditions, and the degree of preferred orientation can be clearly determined even for week orientation.

Figure 9:
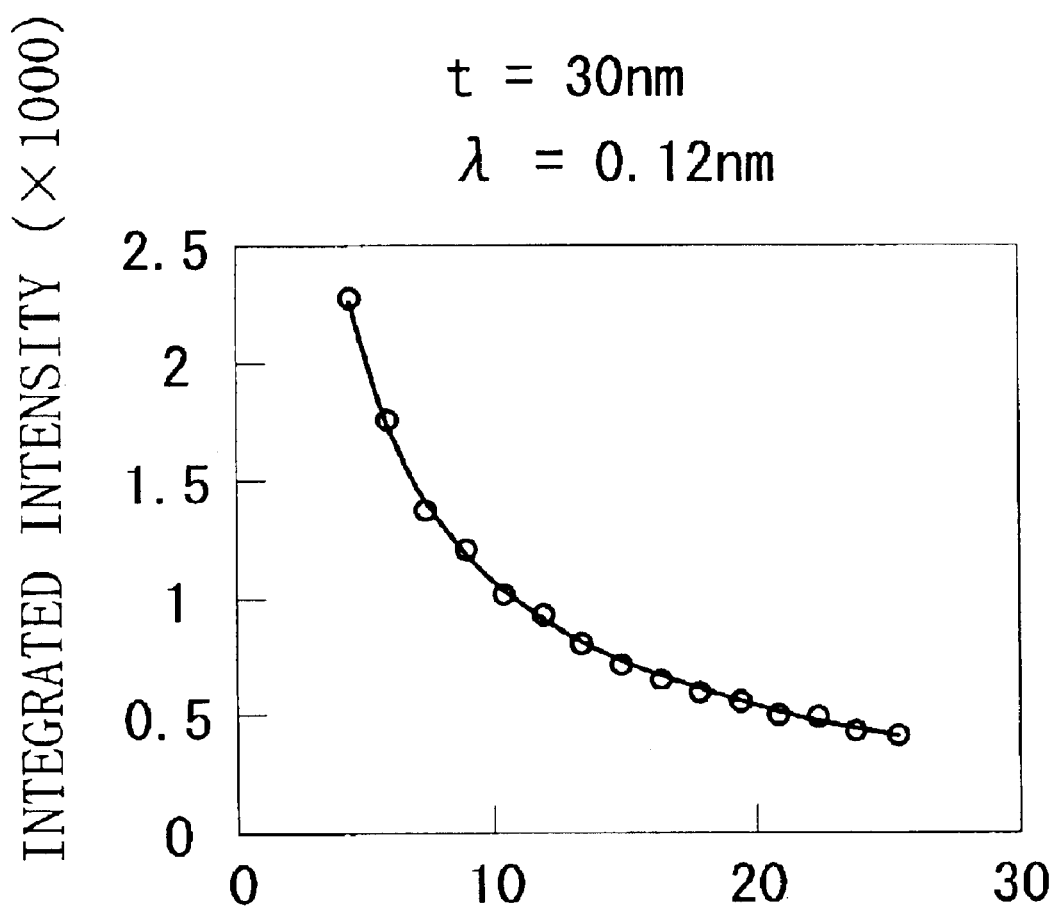
FIG. 9 is a graph of a measurement for the (111) reflection of an Au thin-film with a thickness of 30 nm.

FIG. 9 is similar to FIG. 8 except that the film thickness is 30 nm. In this case, the full width of half maximum H is 81°. Comparing the rocking curves of FIGS. 8 and 9, it can not been apparently seen which curve shows stronger preferred orientation and how strong the preferred orientation is. On the contrary, according to the present invention, H becomes 30.9° for FIG. 8 and 81° for FIG. 9. Thus, it can be easily seen that the curve of FIG. 8 has stronger orientation, the orientation density distribution function being sharp. Thus, the preferred orientation can be quantitatively determined even if the preferred orientation is weak, i.e., in the case where it can not be apparently seen whether the material is oriented or not by observation of a rocking curve.

This is a significant advantage as compared with the conventional methods.

Figure 10:
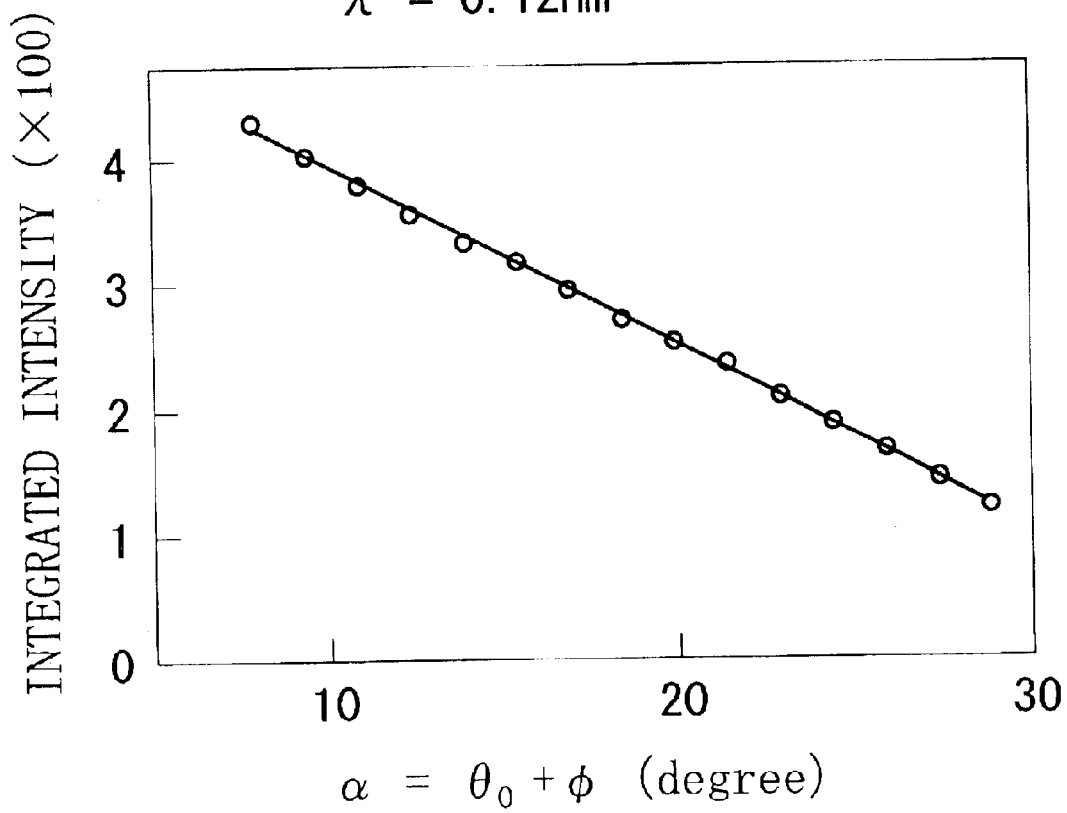
FIG. 10 is a graph of measurement for the (220) reflection of $CeO_2$ powder.

FIG. 10 is a graph of a measurement for the (220) reflection of $CeO_2$ powder (cerium oxide, NIST SRM674). The X-ray source is a synchrotron radiation and an X-ray with a wavelength of 0.12 nm is taken out. The Bragg angle $\theta_0$ is 18.28°. The powder is oriented at random. The theoretical rocking curve, which becomes a straight line, can be highly fitted to the measurements, blank circles. Thus, the measurement data and the theoretical values are highly in agreement with each other for the sample oriented at random. Accordingly, it is seen that the reliability of the method of the present invention is high.

Figure 11:
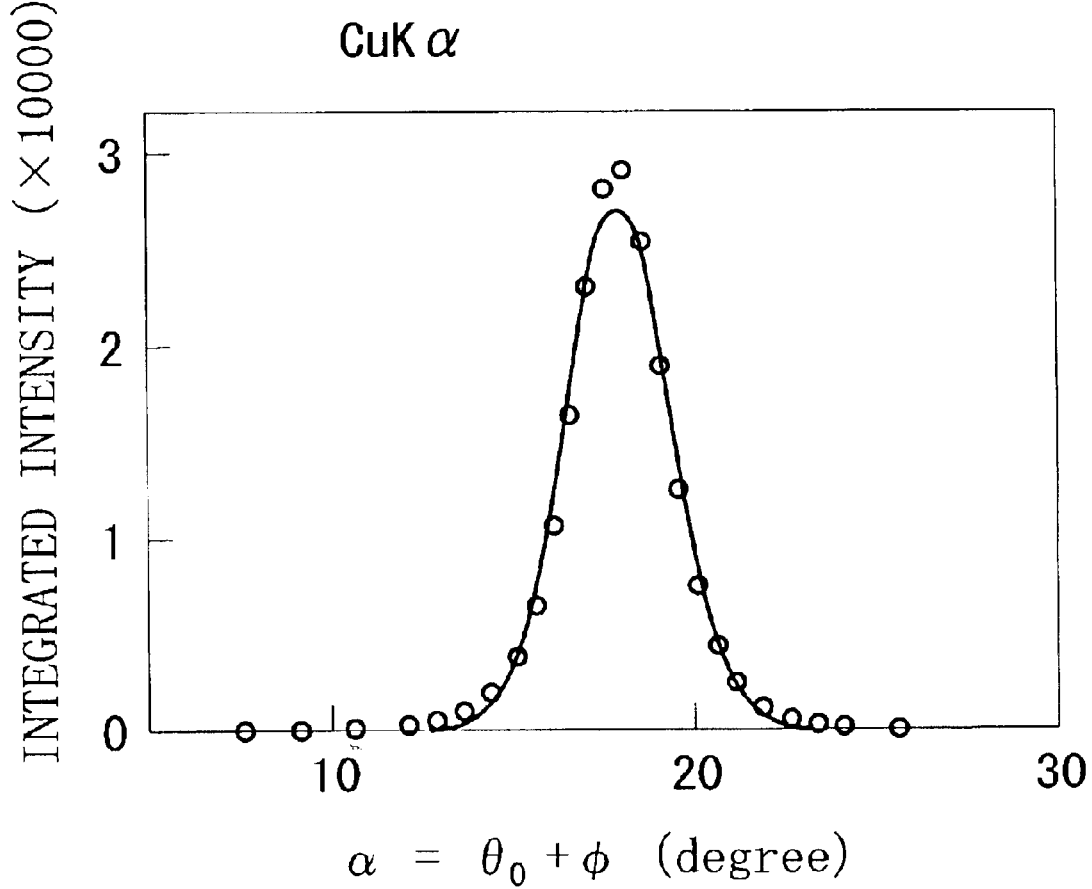
FIG. 11 is a graph of a measurement fort he (002) reflection of an AlN thin film.

FIG. 11 is a graph of a measurement for the (002) reflection of a polycrystalline thin film of AlN, aluminum nitride, formed by sputtering on a glass substrate. The X-ray source is $CuK\alpha$ rays which are made monochromatic with an Si/W multi-layer film mirror. The Bragg angle $\theta_0$ is 18.04°. The orientation density distribution function $\rho(\phi)$ is assumed to be a Gaussian function. The blank circles represent the measurements and the solid line is a theoretical rocking curve, similarly to FIG. 8. It can be seen that this sample is highly oriented by solely observation of the rocking curve. According to the present invention, the full width of half maximum H of the Gaussian distribution of the orientation density distribution function becomes 3.32°. Thus, it is quantitatively ascertained that the material is highly oriented. In this case, calculating the volume fraction v quantitatively, as seen in the lowest lines of the list in FIG. 14, 93.8% of crystallites forming the polycrystalline film have the [001] direction which exist within the range of the angle $\Theta=3.32°$ around the normal of the sample surface.

FIG. 14 shows different measurement results for the different orientation density distribution function, the Gaussian function and the March-Dollase function. The list shows the resultant characteristic parameters, the full width of half maximum H for the Gaussian function, and the preferred orientation coefficient r for the March-Dollase function, and the resultant Bragg angles $\theta_0$. The Bragg angle $\theta_0$ may be handled as a constant, or may be handled as a variable in addition to the characteristic parameter so that curve-fitting can be accurately carried out. The list in FIG. 14 shows the resultant Bragg angles $\theta_0$ when they are handled as variables. The list shows also the volume fractions v for the two types of the orientation density distribution functions. These values are obtained by calculation, with the use of equation (1), of the existence ratio of crystallites having normal vectors in the range up to the full width of half maximum H of the Gaussian function with respect to the angle $\phi$. Thus, according to the present invention, once the orientation density distribution function $\rho$ has been determined, the volume fraction v also can be quantitatively determined.

In the measurement examples of FIG. 14, for the Au thin films, two types of measurements are obtained for the same sample, with the use of synchrotron radiation with $\lambda=0.12$ nm and $CuK\alpha$ rays from an X-ray tube. In this case, the resultant two values of the full widths of half maximum H of the Gaussian function are in agreement with each other within an experimental error tolerance, irrespective of the types of the X-ray sources. That is, for the thickness of 30 nm, H is equal to 81° for $\lambda=0.12$ nm and is equal to 89° for the $CuK\alpha$ rays. Both are almost the same. Similarly, for the thickness of 50 nm, H is 30.9° and 32.3°, almost the same. As seen in the above-description, even if the measurement systems are different, the absolute estimation of preferred orientations is almost the same according to the present invention. It should be noted in FIG. 4 that although the values of H and v include standard errors, i.e., experimental errors. The error values are not shown. The value of the standard error would be minimum place orders of the listed values. Similarly, it should be noted that the measurement examples of FIG. 20 and FIG. 21, which are described below, would include standard errors.

Figure 12:
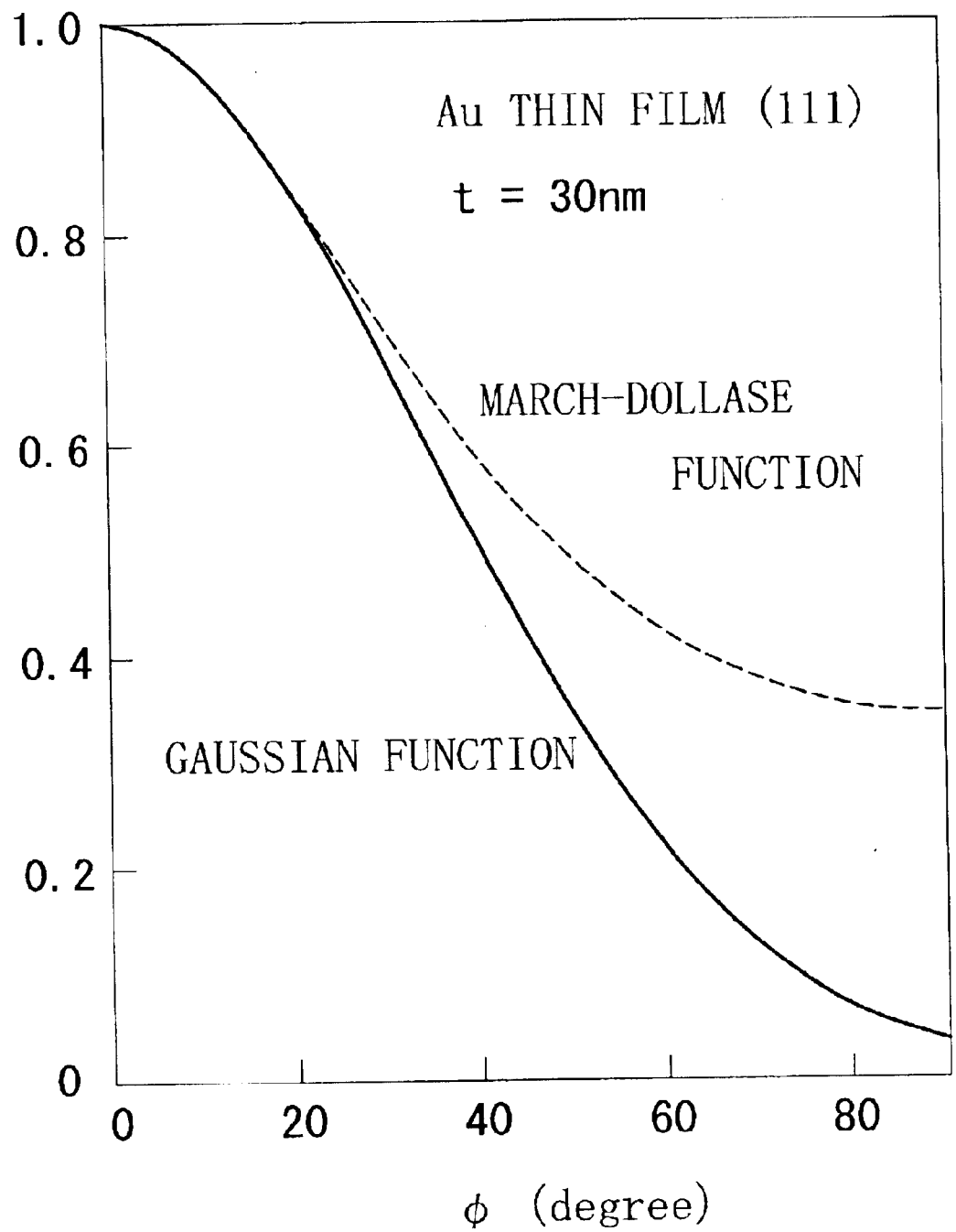
FIG. 12 is a graph of the orientation density distribution function corresponding to FIG. 9.
Figure 13:
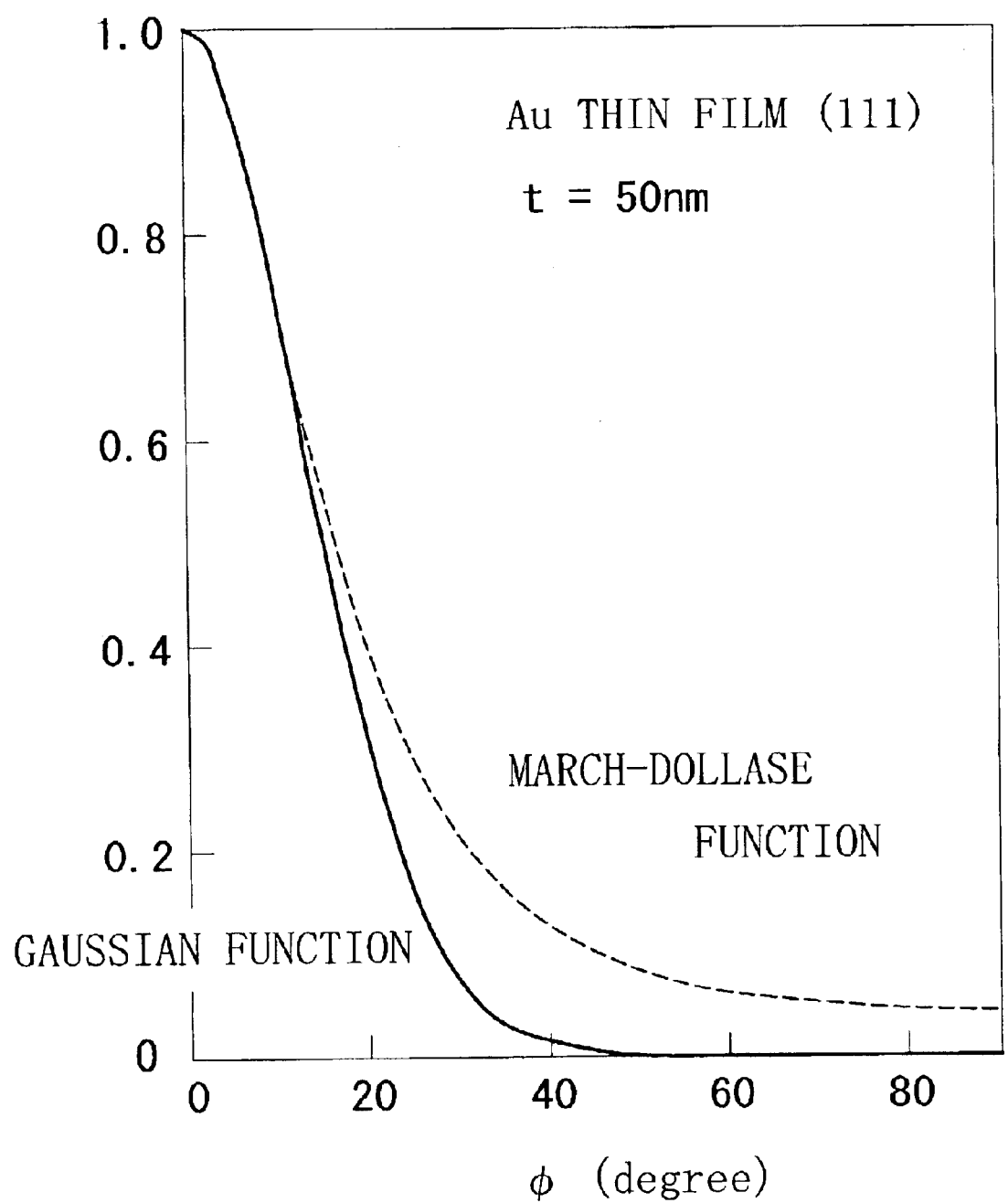
FIG. 13 is a graph of the orientation density distribution function corresponding to FIG. 8.

FIG. 12 shows the specific forms of the Gaussian function and the March-Dollase function which correspond to the measurement example of FIG. 9. Then, FIG. 13 shows the specific forms of the Gaussian function and the March-Dollase function which correspond to the measurement example of FIG. 8.

In the above-described measurement examples, the preferred orientations are estimated assuming that the orientation density distribution function $\rho(\phi)$ does not depend on the depth from the surface of a sample. However, in practical samples, it is expected that the orientation density distribution function changes in the direction of the depth of a sample. Accordingly, an improved estimation method will be described below for the case in which it is assumed that the orientation density distribution function changes depending on the depth from the surface of a sample.

Figure 15A:
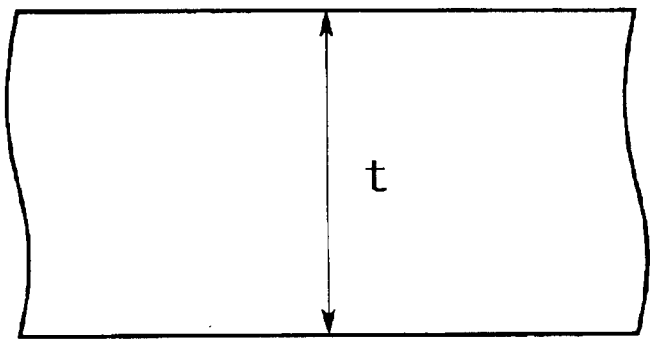
FIG. 15a, FIG. 15b, and FIG. 15c illustrate a single layer model, a two-layer model, and a multi-layer model, respectively.
Figure 15B:
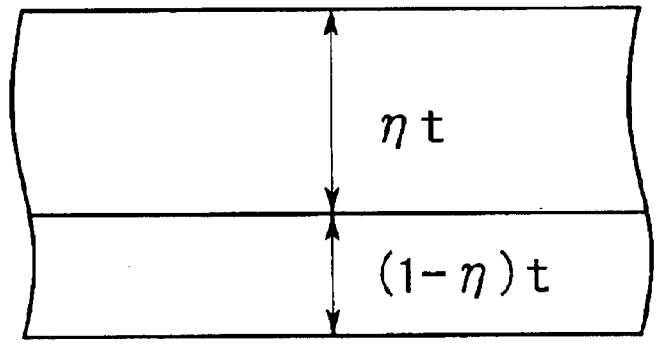
Figure 15C:
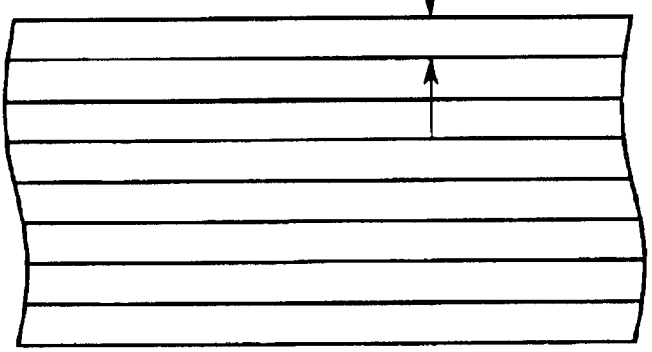

FIGS. 15a, 15b, and 15c show three types of models with respect to the change of the orientation density distribution function in the direction of the depth of a sample. The single layer model of FIG. 15a is that the orientation density distribution function is uniform over the thickness t of a sample. In this case, preferred orientation can be estimated by the above-described method.

FIG. 15b shows a two-layer model in which a sample is divided into an upper layer and a lower layer. Assuming the thickness of the sample to be t, the thickness of the upper layer becomes $\eta t$ while the thickness of the lower layer becomes $(1-\eta)t$. The $\eta$ is in the range of 0 to 1. The orientation density distribution function $\rho(\phi)_U$ for the upper layer is different from the orientation density distribution function $\rho(\phi)_L$. The diffraction intensity expressed by equation (9) in FIG. 5 is changed to equation (14) in FIG. 16. Here, $V_U$ and $V_L$ are expressed by equations (15) and (16) respectively. In this two-layer model, $\eta$ is added as another variable in determining the theoretical rocking curve as compared with the case of the single layer model. Thus, the theoretical rocking curve can be more accurately fitted to the measurement rocking curve.

FIG. 15c shows a multi-layer model in which a sample is divided into a plurality of layers at the same intervals in the vertical direction. Assuming the thickness of the sample to be t and the number of the layers to be N, the thickness $\Delta t$ of each layer becomes $t/N$. The orientation density distribution functions $\rho(\phi)$ for the respective layers, where $m=1$ to N, are assumed to be different from each other. In this case, the diffraction intensity expressed by equation (9) in FIG. 5 is changed to equation (17) in FIG. 17. Here, $V_m$ is expressed by equation (18). In the case of the multi-layer model, since many orientation density distribution functions must be determined, the calculation processing for fitting the theoretical rocking curve to the measurement rocking curve would be remarkably increased if all the characteristic parameters for the respective orientation density distribution functions are arbitrarily changed. Then, from the practical standpoint, the calculation processing is carried out assuming that the characteristic parameters of the respective orientation density distribution functions are changed in a predetermined relation to each other, e.g., the parameters are linearly changed depending on the depth.

Hereinafter, an example of estimation of preferred orientation will be described for the two-layer model with reference to the case in which the orientation density distribution function is a Gaussian function by way of an example. For the two-layer model, in the Gaussian function of equation (2), the full width of half maximum H, which is a characteristic parameter, is $H_U$ for the upper layer and $H_L$ for the lower layer. Also, the $\eta$ in FIG. 15b is assumed to be a variable. The theoretical rocking curve is prepared under the above-described conditions. Then, $\eta$, $H_U$, and $H_L$ are determined so that the theoretical rocking curve can be most closely fitted to the measurement rocking curve. FIG. 18 shows the theoretical rocking curve obtained as described above. The blank circles represent the measurement rocking curve. The measurement sample and the measurement conditions are the same as those for the graph of FIG. 11, single layer model. Accordingly, in FIG. 11 and FIG. 18, the blank circles representing the measurement rocking curve are at the same positions, while the best-fitted theoretical rocking curves are different from each other. It is seen that the theoretical rocking curve of FIG. 18 is more closely fitted to the measurement rocking curve. In the two-layer model of FIG. 18, $\eta=0.59$, $H_U=2.81°$ and $H_L=5.67°$ are obtained. That is, as compared with $H=3.32°$ obtained for the single layer model, the upper layer is more strongly oriented, while the lower layer is weakly oriented.

Figure 19:
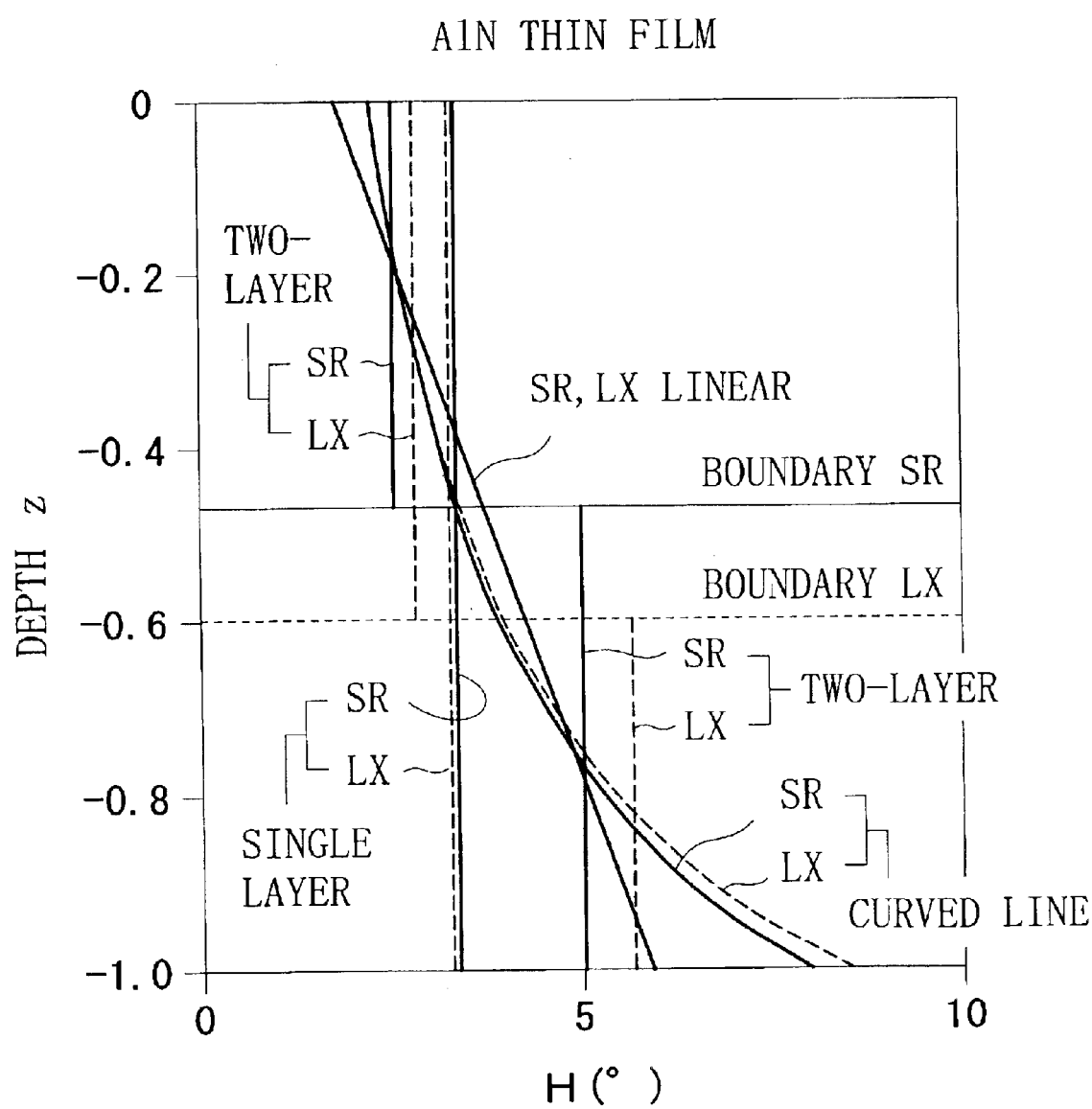
FIG. 19 is a graph showing the estimation results of the preferred orientation for the single layer model, the two-layer model and the continuous layer model.

FIG. 19 is a graph of measurement examples showing the estimation results of the preferred orientation of an AlN thin film sample for the single layer model, the two-layer model and the continuous model, assuming that the orientation density distribution function is the Gaussian function. The full width of half maximum H (°), which is a characteristic parameter of the Gaussian function, is plotted as abscissa. The depth z from the surface of a sample is plotted as ordinate. The depth z, which is below the surface of the sample, is expressed as a negative value and is normalized by the thickness t of the sample. That is, when the depth z is t which is the thickness of the sample, the bottom of the thin film, it is expressed by minus 1.0. The continuous model is equivalent to the model in which N of the multi-layer model in FIG. 15c becomes infinity. In the case in which the Gaussian function is used, the full width of half maximum H is assumed to be continuously changed depending on the depth. Equation (19) in FIG. 17 is for a linear model of the continuous model in which the full width of half maximum $H_m$ is assumed to be a first-degree function (straight-line relationship) of the depth $Z_m$. Equation (2) is for a curved line model in which the full width of half maximum $H_m$ is assumed to be a minus first-degree function (curved line relationship) of the depth $Z_m$. Then, a, b, c, and d in equations (19) and (20) are coefficients of the first-degree function and the minus first-degree function, and are characteristic parameters to be determined.

In the graph of FIG. 19, SR represents the fitting of the theoretical rocking curve to the measurement results obtained with the use of a synchrotron radiation as the X-ray source. LX represents the fitting of the theoretical rocking curve to the measurement results obtained with the use of a laboratory X-ray tube, CuKα rays, as the X-ray source. The SR is shown by a solid line, while the LX is shown by a broken line.

In the single layer model, the full width of half maximum H is constant wholly in the depth direction. H is 3.38° for SR and 3.32° for LX. In the two-layer model, $H_U$ is 2.59° for SR and 2.81° for LX in the upper layer, while HL is 5.03° for SR and 5.67° for LX in the lower layer. Regarding the boundary between the upper and lower layers, the $\eta$ value in FIG. 15b is 0.47 for SR and 0.59 for LX. Selecting the two-layer model, the full width of half maximum for the upper layer becomes smaller than that of the single layer model, while the full width of half maximum for the lower layer becomes larger than that of the single layer model.

In the case of the linear model of the continuous model, i.e., using equation (19) in FIG. 17, the H value is linearly changed. As the depth is increased, the H becomes larger. The SR and the LX approaches each other so as to be substantially the same in the graph. The values of a and b in equation (19) are listed in the table of FIG. 21. Also, in the case of the curved line model of the continuous model, that is, using equation (20) in FIG. 17, the H value is changed in a curved line pattern depending on the depth. Also, as the depth is increased, the H becomes larger. The values of c and d in equation (20) are listed in the table of FIG. 21.

FIG. 20 lists the estimation results of the single layer model and the two-layer model which are shown in the graph of FIG. 19. In this list, Rp and Rwp are estimation indexes which represent the agreement degrees of fitting between the measurement rocking curve and the theoretical rocking curve, and are defined by equations (21) and (22) in FIG. 22, respectively. The method of minimizing equation (21) is so-called the method of least squares. In these equations, f(x) represents the theoretical rocking curve, y is an observational value, and w is a statistical weight. In the embodiments of the present invention, w is assumed to be 1/y.

The theoretical rocking curve is fitted to the measurement rocking curve so that the estimation indexes are minimized. The table of FIG. 20 shows so-determined estimation index values. Comparing the single layer model and the two-layer model, both of $R_p$ and $R_{wp}$ are considerably small in the two-layer model. Thus, it can be seen that when the two layer model is employed, the theoretical rocking curve is more closely in agreement with the measurement rocking curve. This is the same as has been described in comparing the graphs of FIG. 11 and FIG. 18.

FIG. 21 is a list of the estimation results of the linear model and the curved line model which are shown in the graph of FIG. 19. The $R_p$ and the $R_{wp}$ are the same as the estimation indexes defined in conjunction with FIG. 20. Comparing the tow-layer model and the continuous model, the obtained values of the estimation indexes are generally not significantly different from each other. Accordingly, in this measurement example, it can be seen that a sufficient estimation accuracy can be obtained even with the use of the two-layer model.

According to the present invention, a preferred orientation can be quantified in a wide range from weak orientation to strong orientation, using the same theoretical formulas. The dependence on measurement apparatus and measurement conditions are small, and thus the quantified values can be generalized. Diffraction intensity curves, rocking curve, attained by X-ray diffraction apparatus in a wide application field such as powder diffractometers, thin film diffraction apparatus and so forth can be utilized. The measurement results of preferred orientation can be unified. Thus, the method of the present invention can be used as an estimation tool for material development.

In the above-described embodiments, the integrated intensity is measured, as shown in FIG. 7, and taken as a diffraction X-ray intensity for the respective incident angles α. However, a peak intensity may be used instead of the integrated intensity as a simplified method, noting that the accuracy is inferior.

What is claimed is:

1. A method of estimating preferred orientation of a polycrystalline material comprising the steps of:

(a) assuming an orientation density distribution function $\rho$ which is axisymmetric on a normal direction of a surface of a sample made of a polycrystalline material, said orientation density distribution function $\rho$ being a function of an angle $\phi$ at which a normal of a measurement lattice plane of a crystallite of the sample is inclined to the normal of the surface of the sample, and said orientation density distribution function $\rho$ containing a characteristic parameter characterizing a form of the function;

(b) measuring an intensity of a diffraction X-ray incident upon the surface of the sample at an incident angle $\alpha$ and reflected from said measurement lattice plane of the sample, and determining a change of the intensity of the diffraction X-ray from said measurement lattice plane with the incident angle $\alpha$ being changed to obtain a measurement rocking curve, wherein the diffraction X-ray from the measurement lattice plane has an angle $2\theta_0$ to an incident X-ray, and the incident angle $\alpha$ has a relationship of $\alpha=\theta_0+\phi$;

(c) calculating a theoretical diffraction X-ray intensity based on said orientation density distribution function $\rho$ to obtain a theoretical rocking curve including said characteristic parameter; and (d) determining said characteristic parameter so that said theoretical rocking curve approaches said measurement rocking curve as closely as possible, whereby said orientation density distribution function $\rho$ is determined.

2. A method according to claim 1, wherein said orientation density distribution function $\rho$ is integrated from zero to a desired angle $\Theta$ with respect to the inclination angle $\phi$ so that there can be determined a volume fraction of crystallites with which the normal of the measurement lattice plane exists within a range of the angle $\Theta$ around the normal direction of the surface of the sample.

3. A method according to claim 1, wherein said orientation density distribution function $\rho$ depends on a depth from the surface of a sample.

4. A method according to claim 3, wherein in a case of a sample assumed to be divided into an upper layer and a lower layer, said orientation density distribution function $\rho$ comprises a first function, which does not depend on the depth within the upper layer, for the upper layer, and a second function, which does not depend on the depth within the lower layer, for the lower layer.

5. A method according to claim 3, wherein in a case of a sample assumed to be divided into a plurality of layers at equal intervals in a vertical direction, said orientation density distribution function $\rho$ comprises respective functions, which do not depend on the depth within each layer, for said plurality of layers.

6. A method according to claim 3, wherein said orientation density distribution function $\rho$ is a Gaussian function and said characteristic parameter linearly changes with the depth from the surface of the sample.

7. A method according to claim 3, wherein said orientation density distribution function $\rho$ is a Gaussian function and said characteristic parameter curvedly changes with the depth from the surface of the sample.

8. A method according to claim 1, wherein said orientation density distribution function $\rho$ is a Gaussian function.

9. A method according to claim 1, wherein said orientation density distribution function $\rho$ is a March-Dollase function.

* * * * *